(12) United States Patent
Blanco (10) Patent No.: US 12,023,046 B2
(45) Date of Patent: Jul. 2, 2024

(54) BONE DUST COLLECTOR DEVICE

(71) Applicant: THE CLEVELAND CLINIC FOUNDATION, Cleveland, OH (US)

(72) Inventor: Guillermo Ortiz Blanco, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 18/120,385

(22) Filed: Mar. 11, 2023

(65) Prior Publication Data

US 2023/0285035 A1 Sep. 14, 2023

Related U.S. Application Data

(60) Provisional application No. 63/318,913, filed on Mar. 11, 2022.

(51) Int. Cl.
*A61B 17/16* (2006.01)
*A61M 1/00* (2006.01)

(52) U.S. Cl.
CPC .......... *A61B 17/1635* (2013.01); *A61M 1/60* (2021.05); *A61M 1/604* (2021.05); *A61M 1/79* (2021.05); *A61B 2217/005* (2013.01)

(58) Field of Classification Search
CPC ......... A61B 17/1635; A61B 2217/005; A61M 1/60; A61M 1/79; A61M 1/604
See application file for complete search history.

(56) References Cited

U.S. PATENT DOCUMENTS

| | | | | |
|---|---|---|---|---|
| 2005/0189288 | A1* | 9/2005 | Hershberger | B09B 3/0075 210/473 |
| 2007/0225665 | A1* | 9/2007 | Perez-Cruet | A61M 1/79 604/317 |
| 2008/0243028 | A1* | 10/2008 | Howard | A61M 1/79 600/565 |
| 2013/0164731 | A1* | 6/2013 | Cimino | A61M 1/88 435/284.1 |
| 2015/0090652 | A1 | 4/2015 | Hensler | |
| 2015/0090654 | A1* | 4/2015 | Hubrig | C02F 1/4608 210/243 |
| 2018/0200419 | A1* | 7/2018 | Locke | A61M 1/98 |
| 2018/0333520 | A1* | 11/2018 | Mills | A61M 1/79 |
| 2018/0344327 | A1* | 12/2018 | Jeng | A61B 17/1635 |

(Continued)

FOREIGN PATENT DOCUMENTS

| WO | 2019239375 A3 | 12/2019 | |
|---|---|---|---|
| WO | 2020053517 A1 | 3/2020 | |
| WO | WO-2020053517 A1 * | 3/2020 | ............... A61M 1/79 |

OTHER PUBLICATIONS

PCT International Search Report and Written Opinion for corresponding application serial No. PCT/US2023/015041, dated Aug. 3, 2023, pp. 1-13.

*Primary Examiner* — Guy K Townsend
(74) *Attorney, Agent, or Firm* — TAROLLI, SUNDHEIM, COVELL & TUMMINO L.L.P.

(57) ABSTRACT

A bone tissue collection device is provided with an exterior collection container and a porous interior filter container. The device includes a lid having an upper face and is configured to releaseably seal the exterior collection container and interior filter container. A suction inlet tube and a suction outlet tube are operably coupled to the lid and angled from the upper face of the lid.

9 Claims, 10 Drawing Sheets

(56) References Cited

U.S. PATENT DOCUMENTS

| | | |
|---|---|---|
| 2019/0167869 A1* | 6/2019 | Willard .................. A61M 1/67 |
| 2023/0074586 A1* | 3/2023 | Verri .................. A61M 1/0281 |
| 2023/0285035 A1* | 9/2023 | Blanco .................. A61M 1/88 |

* cited by examiner

Concentric

FIG. 10

Non-Concentric

FIG. 11

BONE DUST COLLECTOR DEVICE

CROSS-REFERENCE TO RELATED APPLICATION

This application claims priority to U.S. Provisional Application Ser. No. 63/318,913, filed on Mar. 11, 2022, which is hereby incorporated by reference in its entirety.

TECHNICAL FIELD

The present disclosure relates to a bone tissue collection device that is configured to collect autologous bone tissue and filter out non-bone tissue material for spinal fusion surgery.

BACKGROUND

The aging of the spine has significant implications for many individuals and the health care system. With this often-inevitable deterioration, comes the need for spinal correction interventions. In spinal correction surgeries, spinal fusions are often required to ensure full recovery of the patient. While spinal fusion is often associated with the insertion of devices, screws and rods, a core of these surgeries is creating a durable bone fusion between spinal elements. Evidence suggests that the use of autologous bone provides a strong long term, stable fusion. However, conventional techniques often waste significant portions of bone tissue being harvested through lack of preservation or inability to properly separate the bone from other materials in an appropriate time period. As a result, there have been increasing efforts to ensure that all available autologous bone is collected and preserved during all parts of the spinal surgery to be used for this purpose.

SUMMARY

The present disclosure relates to bone tissue collection devices. Fluid collected from drilled bone can move from an inlet tube to an inlet port in the lid of a container, wherein the bone tissue moves to the bottom of the container due to its higher density. Once the container has filled, blood and other irrigation can exit through an outlet port in the lid to an outlet tube. After the harvesting of the bone tissue has been completed, the ports can be closed and an opening in the lid or the container can be exposed to allow drainage of any excess blood or irrigation without contaminating the bone. The remaining collected bone tissue can be well-suited for an autologous bone autograft. In other aspects, ports are not closed, but rather once harvesting of bone tissue is completed, the container can be temporarily detached from the lid. The contents can be emptied and the empty container can be reattached to the lid. At this point, collection of additional bone tissue can resume.

In particular, in an aspect a bone tissue collection device is provided that comprises: a sterile exterior collection container and a sterile interior filter container disposed in the exterior collection container. The interior filter container comprises a plurality of pores extending from an inner surface to an outer surface. A suction inlet tube has one end configured to be in fluid communication with a bone tissue material suction source and another end configured to be in fluid communication with the interior filter container. A suction outlet tube has one end configured to be in fluid communication with a waste suction source and another end configured to be in fluid communication with at least the space between the interior filter container and the exterior collection container. The device further includes a lid having an upper face and configured to releaseably seal the exterior collection container and interior filter container. The suction inlet tube and the suction outlet tube are operably coupled to the lid and angled from the upper face of the lid.

DETAILED DESCRIPTION

As used herein with respect to a described element, the terms "a," "an," and "the" include at least one or more of the described element(s) including combinations thereof unless otherwise indicated. Further, the terms "or" and "and" refer to "and/or" and combinations thereof unless otherwise indicated. By "substantially" is meant that the distance, shape, or configuration of the described element need not have the mathematically exact described distance, shape, or configuration of the described element but can have a distance, shape, or configuration that is recognizable by one skilled in the art as generally or approximately having the described distance, shape, or configuration of the described element. As such "substantially" refers to the complete or nearly complete extent of a characteristic, property, state, or structure. The exact allowable degree of deviation from the characteristic, property, state, or structure will be so as to have the same overall result as if the absolute characteristic, property, state, or structure were obtained. The terms "top," "bottom," "upper," "lower," "inner," "outer," "exterior," and "interior" refer to the relative position of components as illustrated in the drawings. The sequence of operations (or steps) is not limited to the order presented in the claims, figures, or description unless specifically indicated otherwise. As used herein a "patient" includes a mammal such as a human being. Although the drawings show certain elements of a bone tissue collection device in combination, it should be noted that such elements can be included (or excluded) in other embodiments or aspects illustrated in other drawings. In other words, each of the disclosed aspects and embodiments of the present disclosure may be considered individually or in combination with other aspects and embodiments of the disclosure. All bone tissue collection devices and components as described herein are used for medical purposes and are therefore sterile. Although a bone tissue collection device is described herein mainly with respect to spinal tissue, the device can be used to filter and collect bone tissue from other areas of the body.

Figure 1:
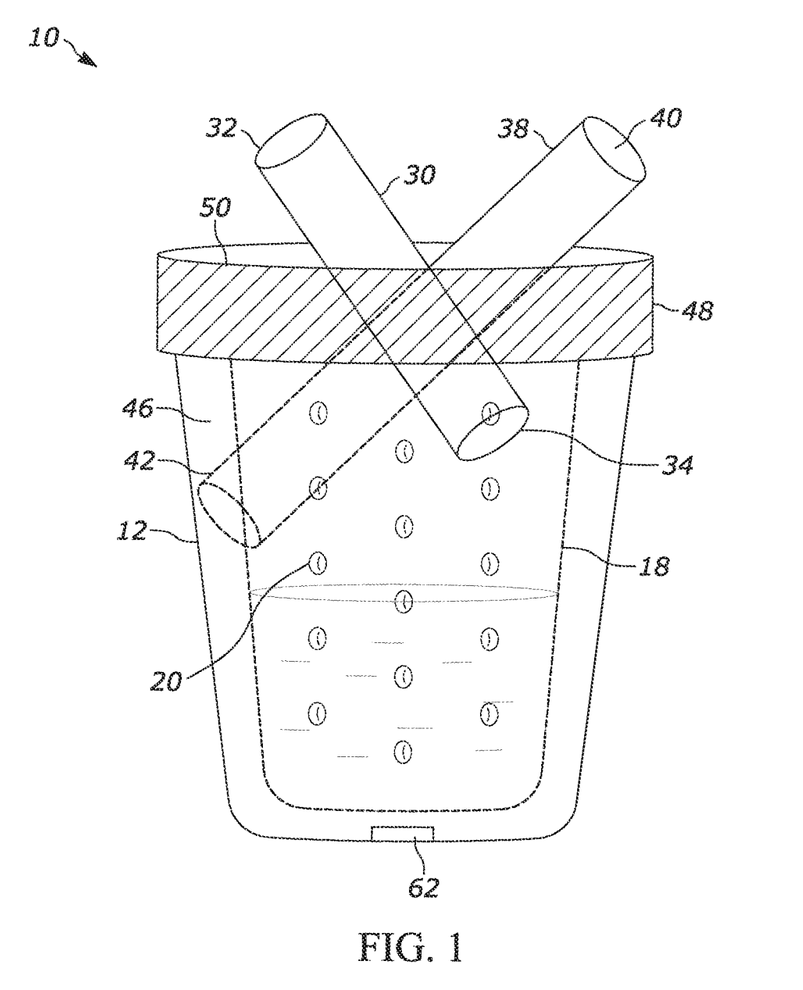
FIG. 1 is a side view of a bone tissue collection device according to an aspect of the present disclosure.
Figure 2:
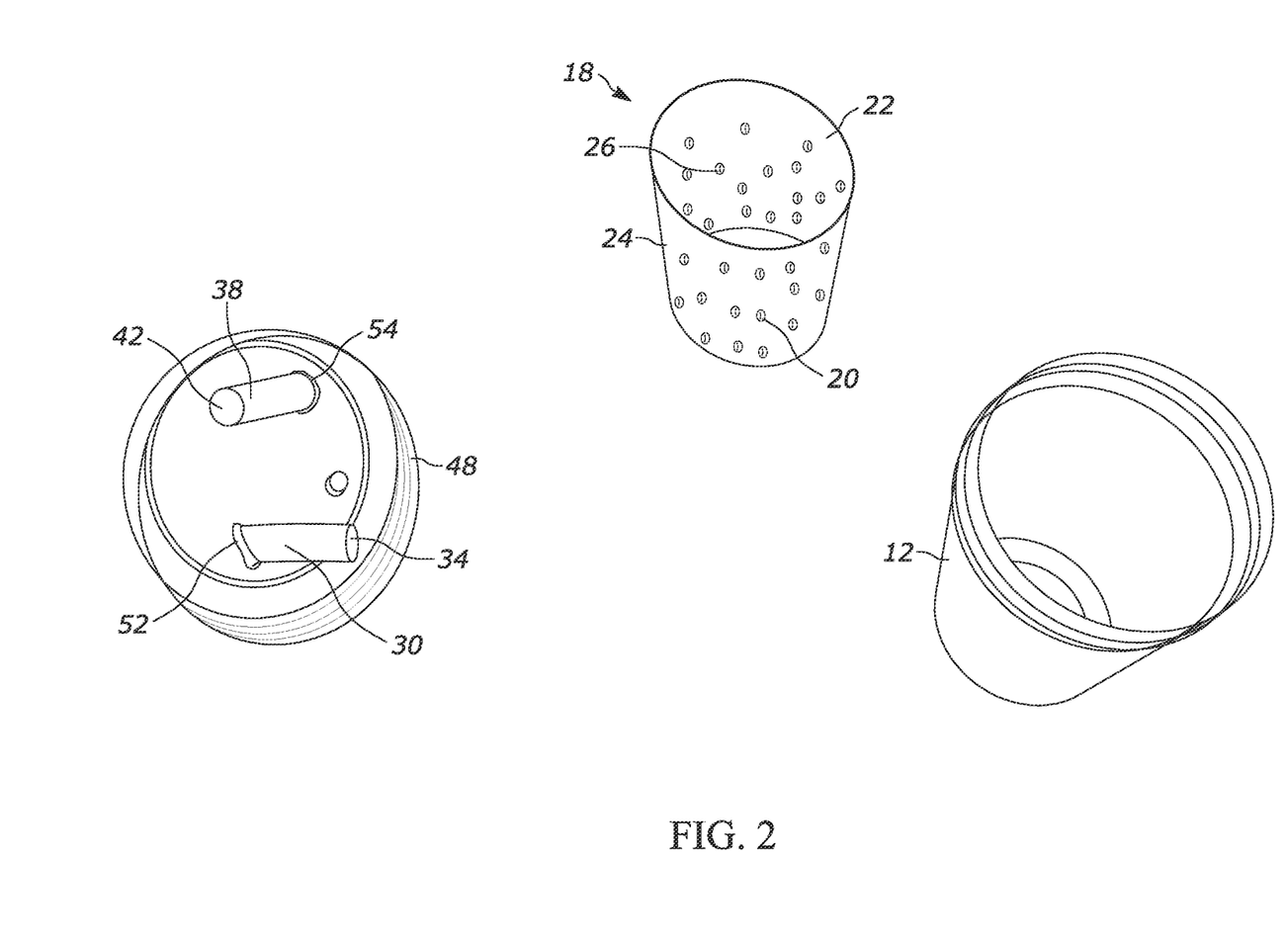
FIG. 2 is a top view of the components of a bone tissue collection device in an un-assembled configuration according to an aspect of the present disclosure.
Figure 3:
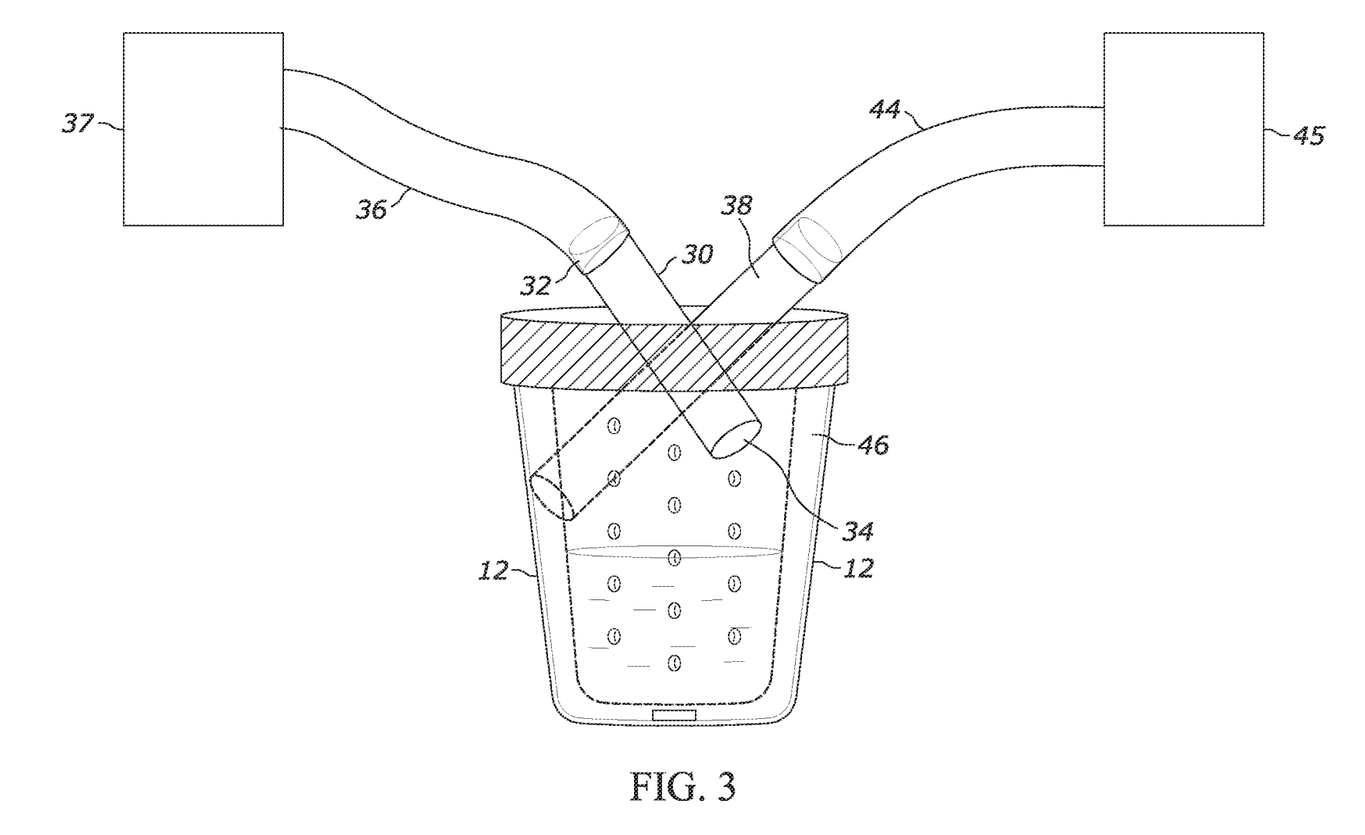
FIG. 3 is a top view of a bone tissue collection device according to an aspect of the present disclosure with the suction inlet tube of the device schematically connected to a bone tissue material suction source and the suction outlet tube of the device schematically connected to a waste suction source.
Figure 4:
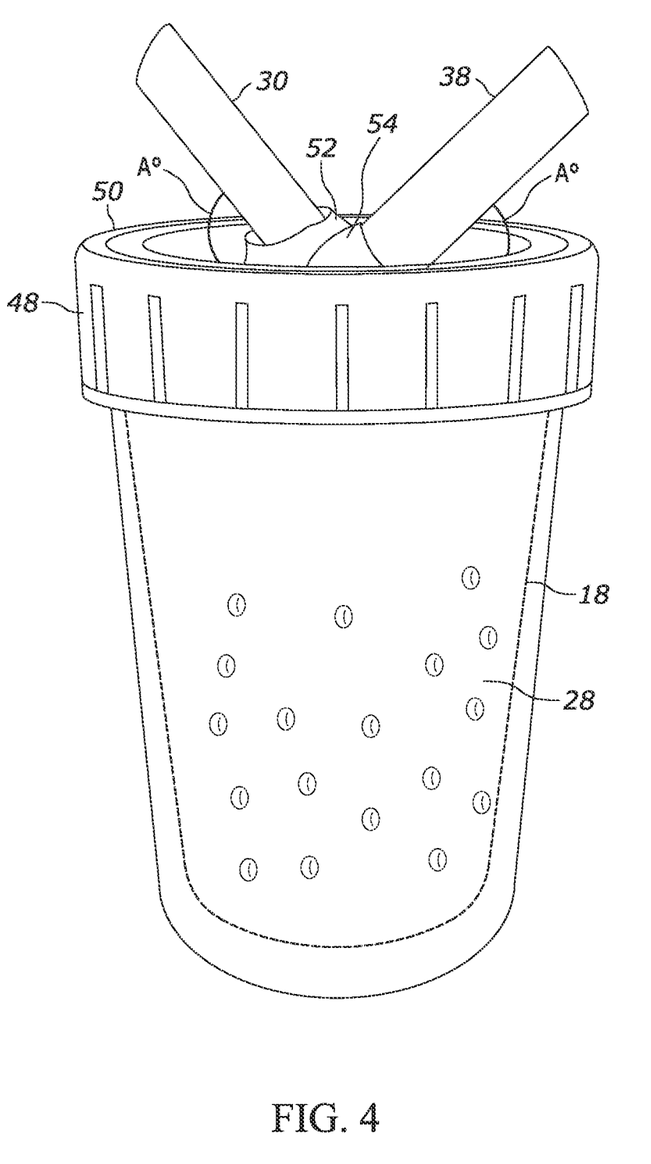
FIG. 4 is side view of a bone tissue collection device according to an aspect of the present disclosure.
Figure 5:
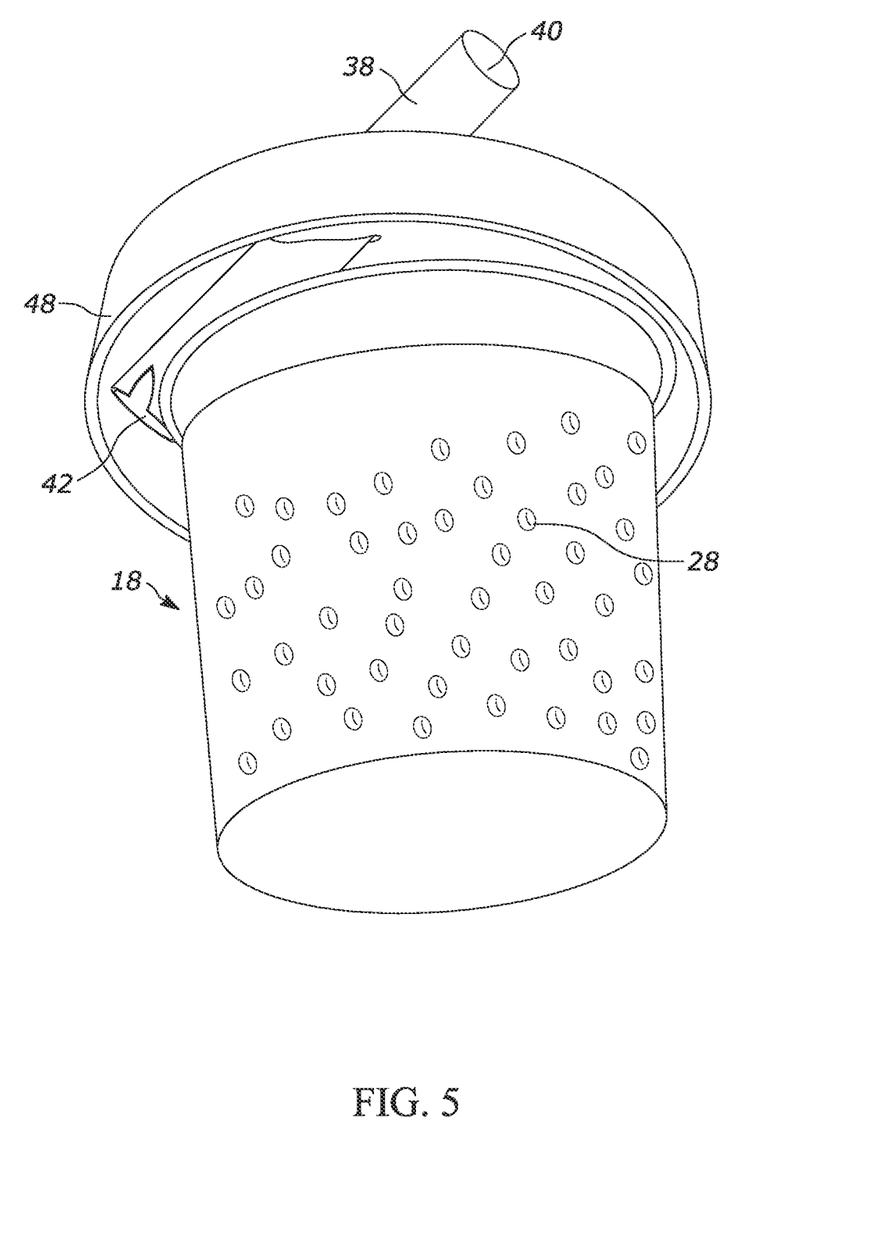
FIG. 5 is a side view of an interior filter container, suction outlet tube, and lid of a bone tissue collection device according to an aspect of the present disclosure.
Figure 6:
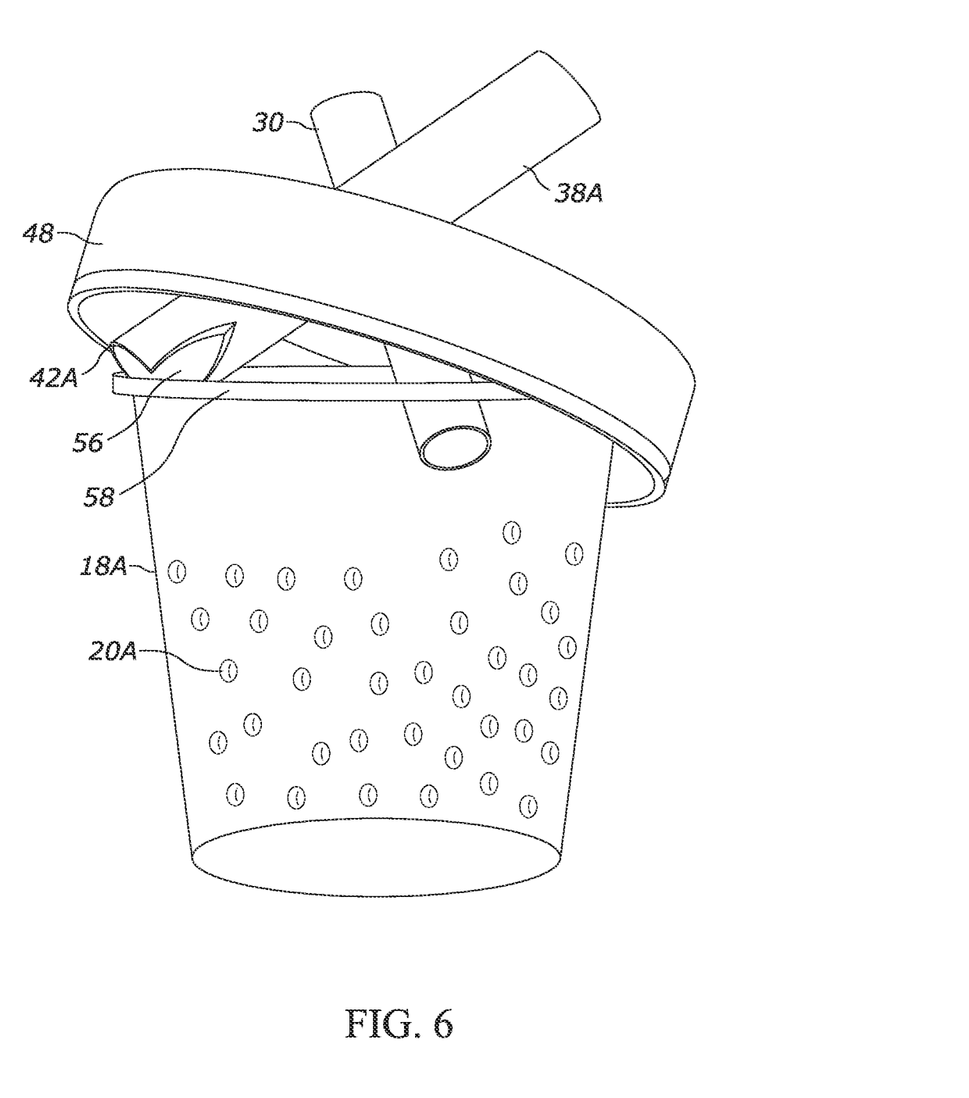
FIG. 6 is side view of an interior filter container, suction outlet tube, and lid of a bone tissue collection device according to an aspect of the present disclosure.
Figure 10:
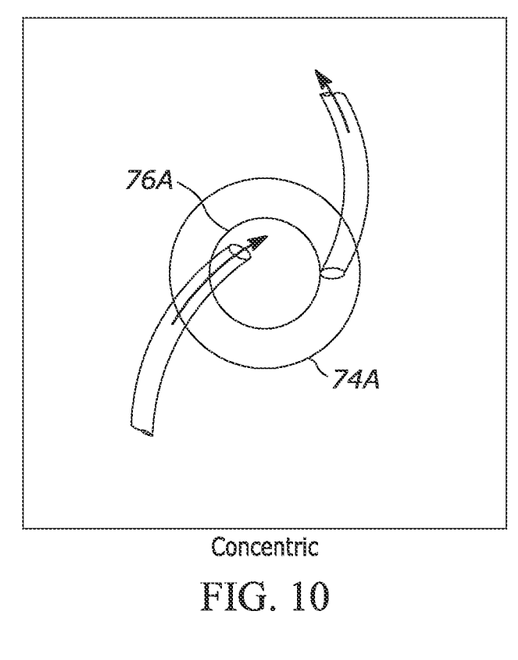
FIG. 10 is a top view bone tissue collection device according to an aspect of the present disclosure.
Figure 11:
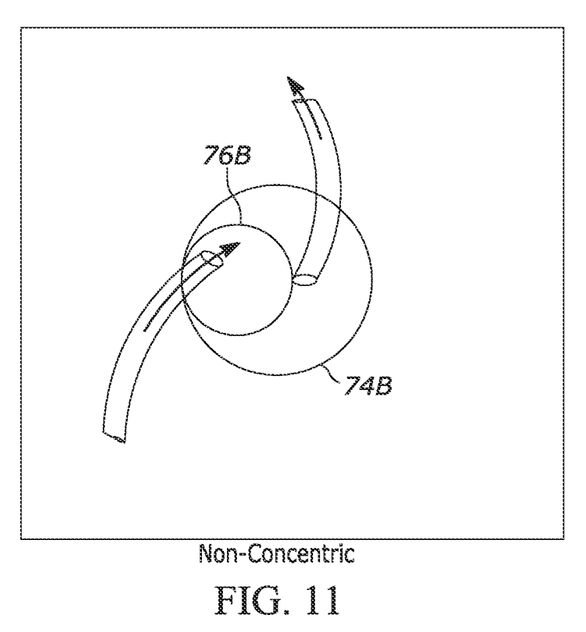
FIG. 11 is a top view bone tissue collection device according to an aspect of the present disclosure.

Referring to FIGS. 1-5, in an aspect bone tissue collection device 10 comprises exterior collection container 12 and interior filter container 18 disposed in exterior collection container 12. Referring to FIG. 1, exterior collection container 12 can have a hydrophilic coating on the inner surface of the container. Exterior container 74 and interior container 76 can be concentric (as depicted in FIG. 10) or non-concentric (as depicted in FIG. 11). With further reference to FIGS. 2 and 4, interior filter container 18 can comprise a plurality of pores 20 extending from inner surface 22 to outer surface 24. Surrounding portions 26 of inner surface 22 defining respective pores 20 can be roughened (e.g. the surrounding portion at the perimeter of a pore can be raised in comparison to the pore itself) as depicted in FIG. 2 and surrounding portions 28 of outer surface 24 defining respective pores 20 can be substantially smooth as depicted in FIGS. 4 and 5. In certain aspects, the size of at least some of the plurality of pores is approximately 0.5 millimeters (mm) to approximately 3 mm. In certain aspects, the interior filter container can be sized and dimensioned to collect approximately 100 cubic centimeter (cc) of material from a bone tissue material suction source. Referring to FIG. 3 in conjunction with FIG. 1, bone tissue collection device 10 can further include suction inlet tube 30 having one end 32 configured to be in fluid communication with a bone tissue material suction source 37 via tubing 36, for example, and another end 34 in fluid communication with interior filter container 18. The bone tissue material that is suctioned can include bone tissue (e.g. autologous bone tissue), fluids (e.g. blood), and other irrigation material (e.g. saline, fat, muscle, ligament, etc.). Bone tissue collection device can also include suction outlet tube 38 having one end 40 configured to be in fluid communication with a waste suction source 45, via tubing 44, for example, and another end 42 in fluid communication with the space 46 between interior filter container 18 and exterior collection container 12, or in fluid communication with interior filter container 18 and exterior collection container 12. When end 42 is in fluid communication with the space between the interior filter container and the exterior collection container, vacuum negative pressure from the waste suction source can draw fluid from the space thereby leaving bone tissue in the interior filter container. Referring to FIG. 6, alternatively, end 42A of suction outlet tube 38A can define a notch or slit 56 that aligns with upper rim 58 of interior filter container 18A in an assembled configuration such that end 42A "straddles" interior filter container 18A. A lid 48 having an upper face 50 can be configured to releaseably seal external collection container 12 and internal filter container 18. Referring to FIGS. 2 and 4, suction inlet tube 30 and suction outlet tube 38 can extend through respective inlet and outlet ports 52 and 54 in lid 48. The suction inlet tube and suction outlet tube can be integral with the lid (e.g. molded as a single piece). Referring back to FIG. 1, a bone tissue collection device can further include removable plug 62 or similar structure disposable in an opening of a bottom surface of the exterior collection container to release pressure when emptying the bone tissue from the interior filter container.

Figure 7:
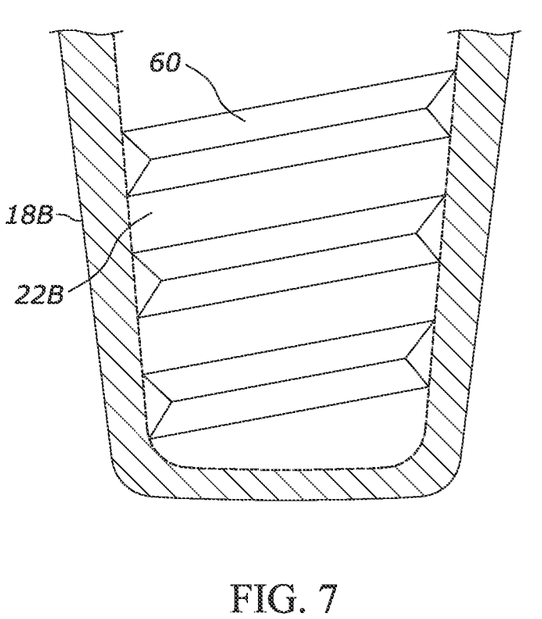
FIG. 7 is a side sectional view of an inner surface of an interior filter container of a bone tissue collection device according to an aspect of the present disclosure.
Figure 9:
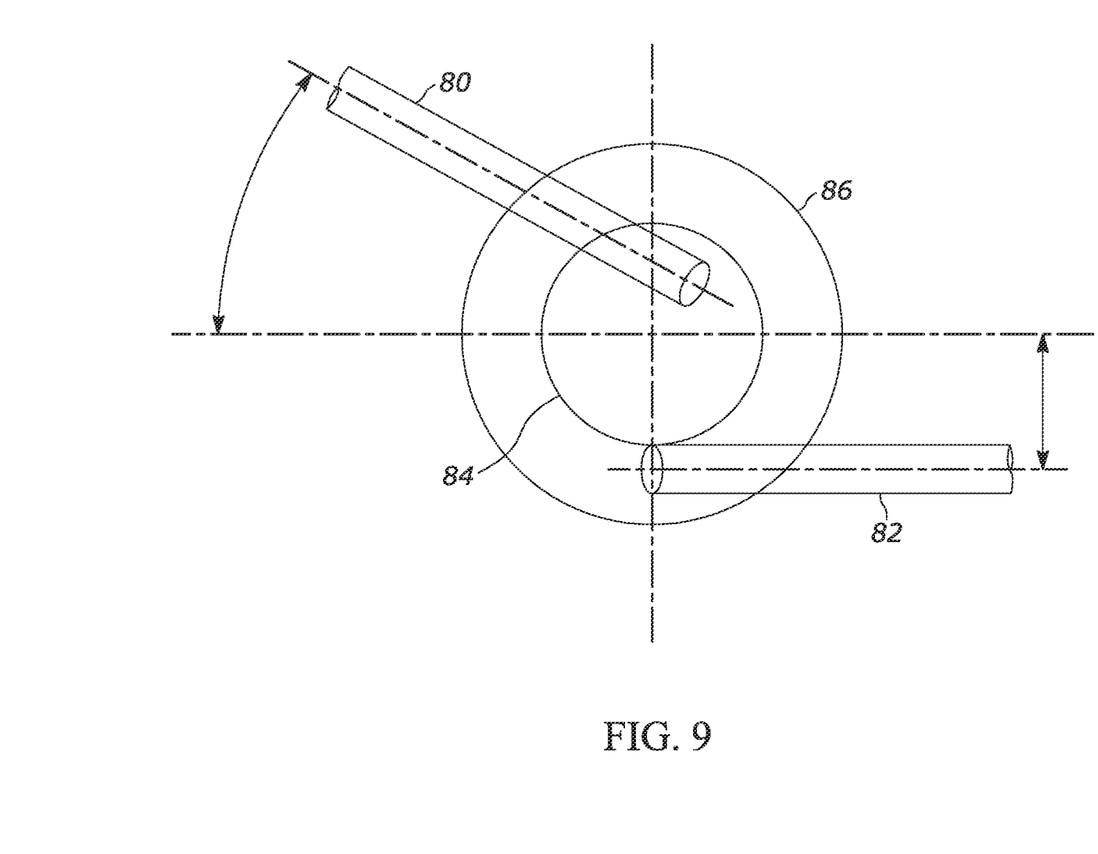
FIG. 9 is a top view bone tissue collection device according to an aspect of the present disclosure.

Referring to FIG. 4, suction inlet tube 30 and suction outlet tube 38 can be operably coupled to lid 48 and angled from upper face 50 of lid 48. Such an angled position of the inlet and outlet tubes can promote helical/cyclone flow of the bone tissue material within the interior filter container leading to laminar (e.g. non-turbulent) flow and efficient compaction of the collected bone tissue along with highly efficient exit of the non-bone tissue material (e.g. blood and other fluid and irrigation material). In particular, such an angled position of the inlet tube can create a circular, cyclone effect whereby the suctioned bone tissue material moves about the inner surface of the interior filter container. Such fluid flow is laminar (non-turbulent) and advantageous as turbulent flow can create shear force that can lead to blood clots. In certain aspects, the suction inlet tube and the suction outlet tube can each be angled approximately 45° (A°) (±20°) from the upper face of the top lid. Suction inlet tube 30 preferably is positioned on the lid such that the flow of irrigation material out of tubing end 34 is tangential to the inner surface of the interior filter container. The suction outlet tube can be opposing the suction inlet tube (e.g. non-parallel). For example and with reference to FIG. 9, inlet tube 80 can be tangential to the inner wall of interior container 84 and outlet tube 82 can be tangential to the inner wall of exterior container 86. Alternatively or additionally and with reference to FIG. 7, inner surface 22B of interior filter container 18B can comprise threading 60 such that the inner surface has a helical or "cork-screw" like surface to direct laminar flow of fluid entering the suction inlet tube into interior filter container 18B.

Figure 8:
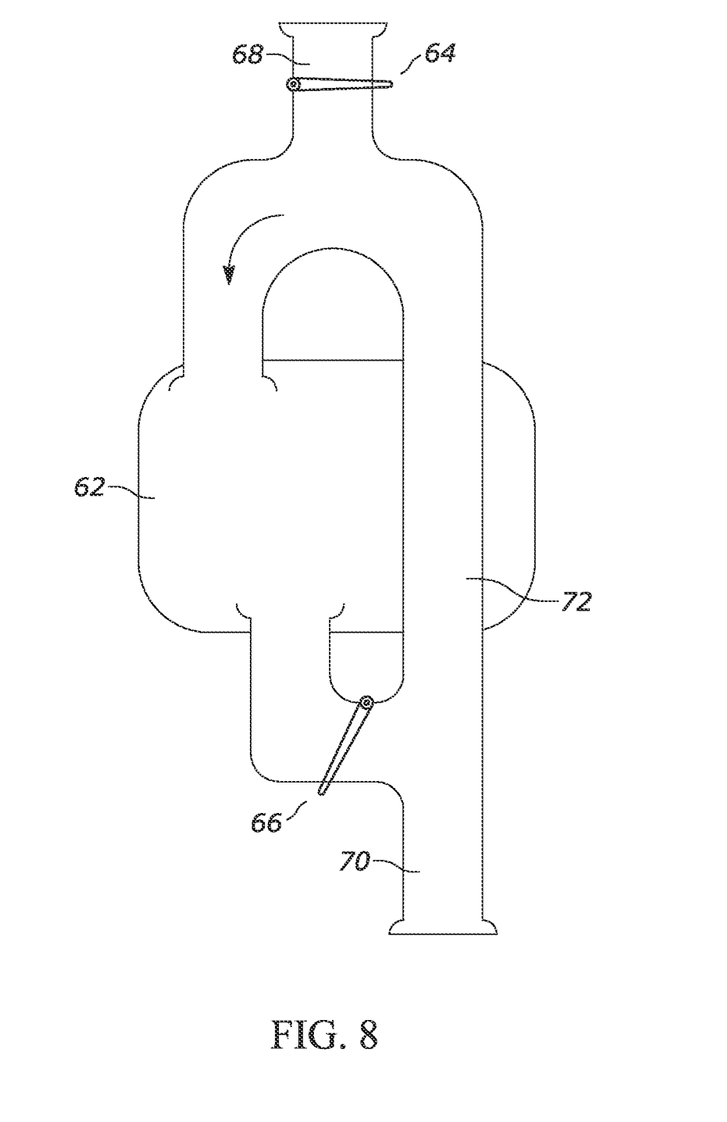
FIG. 8 is a top view of a bypass circuit integrated into a lid of a bone tissue collection device with two valves that allow the user to direct suction contents either through the exterior collection container or directly to the waste suction source (thereby bypassing the exterior collection container).

FIG. 8 schematically illustrates a bypass circuit integrated into lid 62 of a bone tissue collection device with two valves 64 and 66 that allow the user to direct suction contents either through the exterior collection container or directly to the waste suction source (thereby bypassing the exterior collection container). For example, inlet tubing 36 (depicted in FIG. 3) can be connected to suction inlet tube 68", and outlet tubing 44 (depicted in FIG. 3) can be connected to suction outlet tube 70. Valves 64 and 66 can be used reversibly to direct flow of irrigation material to either the exterior collection container or bypass lumen 70 which is in fluid communication with outlet tubing 44 (which in turn is in fluid communication with waste suction source 45 depicted in FIG. 3)

Regarding an exemplary method of using a bone tissue collection device, when drilling bone, a bone tissue collection device can be upright (with the lid positioned above the exterior collection container and interior filter container) to permit collection and filtration of the suctioned bone tissue material. After bone drilling is complete or when a sufficient/significant amount of bone tissue has been collected, the exterior collection container can be quickly removed, emptied and reassembled to the lid. In order to empty the container, once removed from the lid, the exterior collection container together with the interior filter container can be inverted and placed onto a surgical sponge resting on a surgical table, for example, and plug 62 (which can also include a piece of adhesive or a break-away component, for example) can be removed from the opening in the exterior collection container to allow the contents to empty onto the surgical sponge. Alternatively, there can be a first exterior collection container without a bottom opening which is used for collection, and a second exterior collection container with a hole which is used for emptying. In this embodiment, in order to empty the container, once removed from the lid, the contents of the first exterior collection container together with the interior filter container are emptied into the second exterior collection container. The second exterior collection container is then inverted and placed onto a surgical sponge resting on a surgical table, for example. The opening in the bottom of the second exterior collection container allows the contents to empty onto the surgical sponge. In either exemplary device, this step can be performed without interrupting the surgical procedure. This step can be repeated as needed throughout the procedure. When not drilling, or when it is not desired to collect bone tissue, the device can be inverted (the lid can be positioned underneath the exterior collection container) so that suctioned bone tissue can flow from the inlet tube to the outlet tube without being collected.

Each of the disclosed aspects and embodiments of the present disclosure may be considered individually or in combination with other aspects, embodiments, and variations of the disclosure. Further, while certain features of embodiments and aspects of the present disclosure may be shown in only certain figures or otherwise described in the certain parts of the disclosure, such features can be incorporated into other embodiments and aspects shown in other figures or other parts of the disclosure. Along the same lines, certain features of embodiments and aspects of the present disclosure that are shown in certain figures or otherwise described in certain parts of the disclosure can be optional or deleted from such embodiments and aspects. Additionally, when describing a range, all points within that range are included in this disclosure. Further, unless otherwise specified, none of the steps of the methods of the present disclosure are confined to any particular order of performance. Furthermore, all references cited herein are incorporated by reference in their entirety.

What is claimed is:

1. A bone tissue collection device comprising:
 a sterile exterior collection container;
 a sterile interior filter container disposed in the exterior collection container and comprising a plurality of pores extending from an inner surface to an outer surface;
 a suction inlet tube having one end configured to be in fluid communication with a bone tissue material suction source and another end configured to be in fluid communication with the interior filter container;
 a suction outlet tube having one end configured to be in fluid communication with a waste suction source and another end configured to be in fluid communication with at least the space between the interior filter container and the exterior collection container; and
 a lid having an upper face and configured to releaseably seal the exterior collection container and interior filter container, wherein the suction inlet tube and the suction outlet tube are operably coupled to the lid and angled from the upper face of the lid.

2. The bone tissue collection device of claim 1, wherein the suction inlet tube and the suction outlet tube are each angled approximately 45 degrees from the upper face of the top lid.

3. The bone tissue collection device of claim 1, wherein a surrounding portion of the inner surface defining a respective pore of the plurality of pores is roughened and a surrounding portion of the outer surface defining a respective pore of the plurality of pores is substantially smooth.

4. The bone tissue collection device of claim 1, wherein the suction inlet tube and the suction outlet tube extend through respective openings in the lid.

5. The bone tissue collection device of claim 4, wherein the another end of the suction outlet tube is positioned in the space between the interior filter container and the exterior collection container such that vacuum negative pressure from the waste suction source draws fluid from the space thereby leaving bone tissue in the interior filter container.

6. The bone tissue collection device of claim 4, wherein the interior filter container comprises an upper rim and the another end of the suction outlet tube defines a slit or notch that aligns with the upper rim in an assembled configuration.

7. The bone tissue collection device of claim 1, wherein the inner surface of the interior filter container is threaded to direct laminar flow of fluid entering the suction inlet tube into the interior filter container.

8. The bone collection device of claim 1, wherein the size of at least one or more of the plurality of pores is approximately 0.5 millimeters (mm) to approximately 3 mm.

9. The bone tissue collection device of claim 1, further comprising a removable plug disposable in an opening of a bottom surface of the exterior collection container.

* * * * *